(12) United States Patent
Abell et al.

(10) Patent No.: US 12,076,559 B2
(45) Date of Patent: Sep. 3, 2024

(54) DIAGNOSIS AND TREATMENT OF GASTROINTESTINAL DYSFUNCTION VIA IMPLANTATION OF TEMPORARY AND PERMANENT ELECTRICAL STIMULATORS

(71) Applicant: ADEPT-GI, LLC, Louisville, KY (US)

(72) Inventors: Thomas L. Abell, Louisville, KY (US); Douglas E. Parsell, Louisville, KY (US)

(73) Assignee: ADEPT-GI, LLC, Louisville, KY (US)

( * ) Notice: Subject to any disclaimer, the term of this patent is extended or adjusted under 35 U.S.C. 154(b) by 300 days.

(21) Appl. No.: 17/740,852

(22) Filed: May 10, 2022

(65) Prior Publication Data
US 2022/0387792 A1     Dec. 8, 2022

Related U.S. Application Data

(60) Provisional application No. 63/258,891, filed on Jun. 7, 2021, provisional application No. 63/258,895, filed on Jun. 7, 2021.

(51) Int. Cl.
*A61N 1/36* (2006.01)

(52) U.S. Cl.
CPC ..... *A61N 1/36007* (2013.01); *A61N 1/36053* (2013.01); *A61N 1/36139* (2013.01)

(58) Field of Classification Search
CPC ............ A61N 1/36007; A61N 1/36053; A61N 1/36139
See application file for complete search history.

(56) References Cited

U.S. PATENT DOCUMENTS

| | | |
|---|---|---|
| 5,540,730 A | 7/1996 | Terry, Jr. et al. |
| 6,535,764 B2 | 3/2003 | Imran et al. |
| 6,754,536 B2 | 6/2004 | Swoyer et al. |
| 7,016,735 B2 | 3/2006 | Imran et al. |
| 7,020,531 B1 | 3/2006 | Colliou et al. |
| 7,580,751 B2 | 8/2009 | Starkebaum |

(Continued)

FOREIGN PATENT DOCUMENTS

EP     1395169     1/2014

OTHER PUBLICATIONS

Nelson Seabrook MD et al., Inflammatory Markers and Mortality in Diabetic Versus Idiopathic Gastroparesis, The American Journal of the Medical Sciences (Jul. 28, 2021), available at https://doi.org/10.1016/j.amjms.2021.07.013, 26 pages.

(Continued)

*Primary Examiner* — James M Kish
*Assistant Examiner* — Philip C Edwards
(74) *Attorney, Agent, or Firm* — Workman Nydegger

(57) ABSTRACT

Disclosed are gastrointestinal dysfunction treatment protocols and kits for the testing, diagnosis, clinical intervention (diet, medications, temporary gastric electrical stimulation, and/or permanent gastric electrical stimulation), clinical feedback and/or associated treatment parameter adjustment for treating gastrointestinal dysfunctions in a patient. Embodiments of the present disclosure relate to how neuromodulation via gastric electrical stimulation, performed anywhere in the gastrointestinal (GI) tract, can help modulate inflammation and its resultant effects. Modulating inflammation via neuromodulation and gastric electrical stimulation enables treatment of a plurality of gastrointestinal dysfunctions.

31 Claims, 6 Drawing Sheets

(56) References Cited

U.S. PATENT DOCUMENTS

| | | |
|---|---|---|
| 7,630,769 B2 | 12/2009 | Knudson et al. |
| 7,702,394 B2 | 4/2010 | Imran |
| 7,756,582 B2 | 7/2010 | Imran et al. |
| 8,364,269 B2 | 1/2013 | Imran |
| 8,417,342 B1 * | 4/2013 | Abell .................. A61N 1/0509 607/40 |
| 8,792,985 B2 | 7/2014 | Ben-Haim et al. |
| 8,934,975 B2 | 1/2015 | Yaniv et al. |
| 9,037,245 B2 | 5/2015 | Sharma et al. |
| 9,517,152 B2 | 12/2016 | Imran |
| 9,668,690 B1 | 6/2017 | Imran et al. |
| 10,603,490 B2 | 3/2020 | Gifford, III et al. |
| 11,202,907 B2 | 12/2021 | Lo et al. |
| 11,612,749 B2 | 3/2023 | Libbus et al. |
| 11,819,683 B2 | 11/2023 | Goode et al. |
| 11,857,783 B2 | 1/2024 | Lo et al. |
| 2002/0103424 A1 | 8/2002 | Swoyer et al. |
| 2005/0209653 A1 | 9/2005 | Herbert et al. |
| 2006/0247720 A1 | 11/2006 | Starkebaum |
| 2007/0027492 A1 | 2/2007 | Maschino et al. |
| 2008/0065169 A1 | 3/2008 | Colliou et al. |
| 2008/0086179 A1 * | 4/2008 | Sharma ............. A61N 1/36007 607/40 |
| 2010/0249859 A1 | 9/2010 | DiLorenzo |
| 2017/0224986 A1 | 8/2017 | Imran et al. |
| 2019/0240484 A1 | 8/2019 | Goode et al. |
| 2020/0096522 A1 * | 3/2020 | Schorer .................. A61N 1/18 |
| 2020/0306532 A1 | 10/2020 | Grill et al. |
| 2024/0157126 A1 | 5/2024 | Goode et al. |

OTHER PUBLICATIONS

Menzel et al., "Common and Novel Markers for Measuring Inflammation and Oxidative Stress Ex Vivo in Research and Clinical Practice—Which to Use Regarding Disease Outcomes?", Antioxidants, (2021), pp. 1-62.

Cheng et al., "Editorial: Translational Side of Emerging Invasive and Non-invasive Stimulation Therapies", Frontiers in Neuroscience, vol. 16, (Mar. 2022), pp. 1-3.

Bonaz et al., "Therapeutic Potential of Vagus Nerve Stimulation for Inflammatory Bowel Diseases", Frontiers in Neuroscience, vol. 15, (Mar. 2021), pp. 1-16.

Debelle et al., "Impact of Adaptive Gastric Electrical Stimulation on Weight, Food Intake, and Food Intake Rate in Dogs," Artif Organs, vol. 46, No. 6, Jun. 2022, pp. 1055-1067.

"Role of Efferent and Afferent Vagal Nerve Activity During Reproduction: Integrating Function of Oxytocin on Metabolism and Behaviour," to Uvnas-Moberg, Psychoneuroendocrinology, vol. 19, issues 5-7, 1994, pp. 687-695.

* cited by examiner

| Physiologic Parameter | Normal Range | Abnormal Range |
|---|---|---|
| HREM | >185 or <3500 DCI (in mm Hg s cm) | <185 or >3500 DCI |
| GET | < 10% of solid meal at 4 hrs | > 10% of solid meal at 4 hrs |
| EGG | 2.5-3.3 CPM | < 2.5 or > 3.3 CPM |
| EG | 2.5-3.3 CPM | < 2.5 or > 3.3 CPM |
| ANS | TAS | >144 |

FIG. 3

| Biomarkers | Normal Values | Abnormal Values |
|---|---|---|
| CRP (mg/L) | < 3 | > 3 |
| ESR (pg/ml) | >22 M / >29 F | <22 M / <29 F |
| TNFα (pg/ml) | 1.7 – 11.5 | > 11.5 |
| IL-6 (pg/ml) | < 9.3 | > 9.3 |
| IL-8 (pg/ml) | 1 – 5 | > 5 |
| MCP-1 (pg/ml) | 45 – 100 | > 100 |
| MIP-1a (pg/ml) | 10 – 35 | > 35 |
| MI-1b (pg/ml) | 30 – 70 | > 70 |
| Antibodies (pg/ml) | 0.0 | >0.01 |
| GAD-65 (pg/ml) | < 5 | > 5 |

FIG. 4

| | Units | Computation | Initial Energy | 1st Adjustment | Common Energy | Max Enegy |
|---|---|---|---|---|---|---|
| Current Amplitude (I) | milli-amp | | 5 | 10 | 15 | 20 |
| Pulse Width (PW) | micro-sec. | | 330 | 330 | 330 | 450 |
| Rate (hz) | /Sec | | 14 | 14 | 28 | 55 |
| Impedance (Z) | Ohms | | 500 | 500 | 500 | 500 |
| Cycle ON (On) | Sec. | | 0.1 | 1 | 3 | 4 |
| Cycle OFF (Off) | Sec. | | 5 | 4 | 2 | 1 |
| Duty Cycle (DC) % | | ON/(ON+OFF) | 1.96 | 20.00 | 60.00 | 80.00 |

FIG. 5

DIAGNOSIS AND TREATMENT OF GASTROINTESTINAL DYSFUNCTION VIA IMPLANTATION OF TEMPORARY AND PERMANENT ELECTRICAL STIMULATORS

CROSS-REFERENCE TO RELATED APPLICATIONS

This Application claims the benefit of U.S. Provisional Application No. 63/258,895, filed Jun. 7, 2021, and U.S. Provisional Application No. 63/258,891, filed Jun. 7, 2021, which are incorporated herein by reference in their entireties.

BACKGROUND

Technical Field

This disclosure relates to diagnosing and treating gastrointestinal dysfunction with a bioelectric therapy.

Related Technology

Inflammation may underly many disorders, including those of the gastrointestinal (GI) tract. While some GI disorders are identified with inflammation, such as inflammatory bowel disease, the central role of inflammation in other gastrointestinal disorders, such as those presenting as GI motor manifestations, has only recently been recognized. Recently the role of inflammation for disorders such as gastroparesis syndromes, has been detailed.

Patients may present with any number of motility like problems often involving gastrointestinal (GI), nutritional, autonomic and/or systemic symptoms which sometimes include many non-gastrointestinal symptoms. The initial focus for bio-electric therapies is on sign symptoms and findings that may respond to directed therapies. The GI systemic symptoms may include vomiting, nausea, loss of appetite or filling up early, bloating, distension, and abdominal pain. Many patients also have gastro-esophageal reflux/heart burn systemic symptoms, and others have diarrhea and/or constipation. Nutritional symptoms may include weight loss, fluctuations in weight and, in some cases, weight gain. Patient may have tried several dietary changes without improving their GI and/or overall symptoms.

Non-GI symptoms may include symptoms of autonomic nervous system disorders including fainting, weakness, sweating, and heat and cold intolerance. Many patients also have migraine headaches, and some have known or suspected autoimmune diseases such as fibromyalgia or interstitial cystitis. Signs of disorders in some patients may include disorders in gastric emptying of solids and or liquids, with some patients having rapid rather than delayed gastric emptying, measured by any number of techniques. Patients may have disordered motility measurements in not only the stomach but in other areas of the GI tract, including the esophagus, small bowel and/or colon/ano-rectum. Other patients have disordered electrical activity of the stomach or other parts of the GI tract determined by several related electrical measurement techniques. Patients with these disorders may have abnormal biopsies of the GI track lumen or more commonly of the nerves and muscles of deeper GI layers. Associated with these findings can be evidence of systemic inflammation by any number of techniques along with autoimmunity and associated with GI tract microbiome measurements.

SUMMARY

Embodiments of the present disclosure relate to neuromodulation via gastric electrical stimulation, which can be performed anywhere in the gastrointestinal (GI) tract, in order to modulate inflammation and its resultant effects. Modulating inflammation via neuromodulation and gastric electrical stimulation enables treatment of a plurality of gastrointestinal dysfunctions. The details of the methods of how neuromodulation can improve several factors, including inflammation, is expanded below. Gastrointestinal pathologies that are effectively treated with the disclosed treatment process include, but are not limited to, gastroparesis (diabetic, idiopathic and/or post-surgical), inflammatory bowel disease, pancreatitis, gastroesophageal reflux disease, irritable bowel syndrome, chronic constipation, pancreatic (Whipple) procedure induced nausea/vomiting, pregnancy-induced nausea/vomiting, chemotherapy, and/or therapeutic radiation induced nausea/vomiting. Additionally, and/or alternatively, non-gastrointestinal pathologies with vagal-mediated inflammatory aspects, such as atherosclerosis, may also be treated via the disclosed methodology.

Disclosed are gastrointestinal dysfunction treatment protocols, graphically depicted in the form of a flowchart, and kits for the testing, diagnosis, clinical intervention (diet, medications, temporary gastric electrical stimulation, and/or permanent gastric electrical stimulation), clinical feedback and/or associated treatment parameter adjustment for treating gastrointestinal dysfunctions in a patient.

In some embodiments, a method for treating a gastrointestinal dysfunction in a patient is disclosed. In some embodiments, the method includes diagnosing and/or identifying a patient as a suitable candidate for gastric electrical stimulation and placing a temporary gastric/mucosal stimulator in the stomach of the patient. The method may include delivering a first electrical stimulation to the stomach or other part of the GI track via the temporary mucosal stimulator and obtaining an electrogastrogram (EGG) from the temporary stimulator, or other sensor arrays such as an external array positioned cutaneously in direct proximity to the stomach, wherein the electrogastrogram (or similar myogram from elsewhere in the GI tract) comprises electrical signals generated by the stomach or other GI tract organ. The method may further include, based on the obtained electrogastrogram, (i) delivering a second electrical stimulation to the stomach via the temporary gastric stimulator, wherein the second electrical stimulation is of a different energy level, frequency, implantation location and/or amplitude than the first electrical stimulation or (ii) implanting a permanent gastric stimulator in the stomach.

In some embodiments, delivering a first and/or second electrical stimulation to the stomach stimulates the vagus nerve and other autonomic nerves. Stimulating the vagus nerve and related nerves enables propagation of an altered nervous signal to the brain, that more closely mimic nervous system patterns/signals evoked during periods of significantly reduced GI distress, by delivering the altered electrical signal to the desired neurons or nerve network. Additionally, and/or alternatively, stimulating the vagus nerve includes modulating the nerve-conducted electrical pattern from the stomach (or elsewhere in the GI tract) to the brain, thereby treating a gastrointestinal dysfunction in a patient.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIG. 3 is a table with data illustrating the physiologic measurements of GI-related values—normal and abnormal ranges;

FIG. 4 is a table with data illustrating normal and abnormal values of various inflammatory biomarkers;

FIG. 5 is a table with data illustrating typically utilized gastric stimulator energy parameters; which may be similar for other GI Tract locations

DETAILED DESCRIPTION

Figure 1:
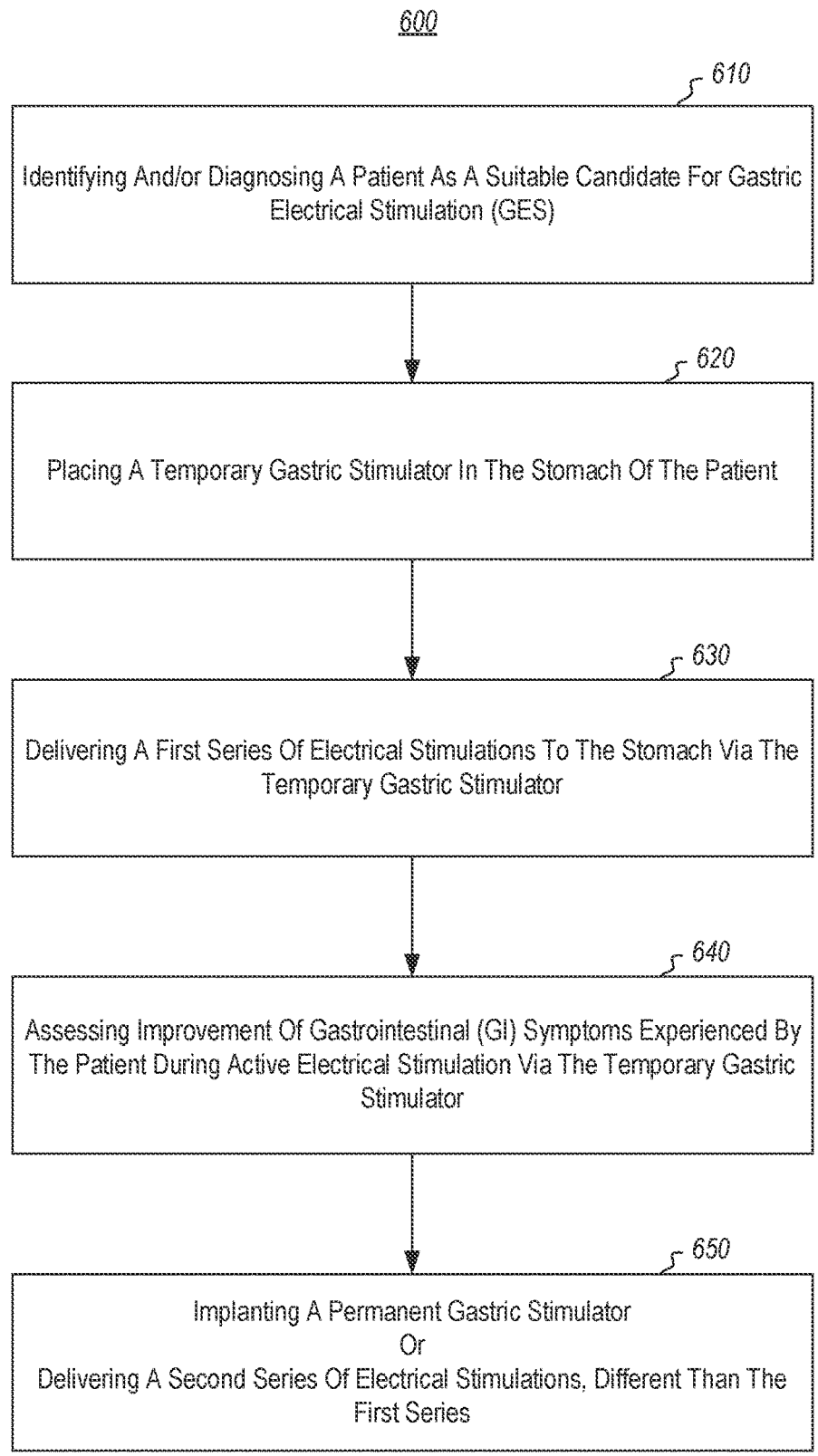
FIG. 1 is a flowchart that illustrates an example method of the present disclosure. This is illustrated for the stomach but can be in other GI Tract locations.

Disclosed are kits, systems, and methods for treating gastrointestinal dysfunction(s) in a patient in need thereof. In some embodiments, a method for treating a gastrointestinal dysfunction includes the steps of identifying the patient as a suitable candidate for gastric (as an example) electrical stimulation (GES); placing a temporary gastric stimulator in the stomach of the patient; delivering a first series of electrical stimulation to the stomach via the temporary gastric stimulator; and assessing whether there is an improvement in gastrointestinal (GI) symptoms experienced by the patient during, for example, periods of active electrical stimulation via the temporary gastric stimulator. It is surprising that neuromodulation via gastric stimulation, anywhere in the GI tract, can help modulate inflammation and its resulting downstream effects. Such neuromodulation via gastric stimulation, surprisingly, treats gastrointestinal dysfunctions and pathologies in patients. Immune mediated pathologies with elements of CNS control via vagal input, such as atherosclerosis, are also treatable pathologies through neuromodulation of gastric organ tissues.

In some embodiments, identifying the patient as a suitable candidate for gastric stimulation includes scoring a GI symptom diary (of the upper, mid and/or lower GI tract) of the patient and implementing a diet and/or medication trial. In some embodiments, identifying the patient as a suitable candidate includes performing medical imaging of target anatomies of the patient and/or performing a gastric emptying and motility study. In some embodiments, a cutaneous and/or mucosal/serosal electrogastrogram (EGG) or related electromyograms elsewhere in the GI tract of the patient's stomach is obtained to identify whether the patient is a suitable candidate. Identifying (or diagnosing) the patient as a suitable candidate may use one or all the aforementioned diagnostic modalities.

In some embodiments, the temporary gastric stimulator may be placed in the stomach via the mucosal lining of the stomach. The temporary gastric stimulator may be secured to the mucosal lining, or other area of the stomach, using clips, anchors and/or sutures. Placing the temporary gastric stimulator in the mucosal lining of the stomach places the stimulator within 0-15 mm, or 0.05-10 mm, of the nerve network of the mucosal lining of the stomach and allows with interface of autonomic nerves including vagal cholinergic and sympathetic adrenergic structures. Such placement of the stimulator may put the stimulator within 0.05, 0.06, 0.1, 0.2, 0.4, 0.6, 0.8, 1.0, 1.2, 1.4, 1.8, 2.2, 2.6, 3, 3.4, 3.8, 4.2, 4.4, 4.6, 4.8, 5.0, 5.2, 5.4, 5.6, 5.8, 6.0, 6.2, 6.4, 6.6, 6.8. 7.0, 7.2, 7.4, 7.5, 8, 10, 12 or 15 mm of the nerve network, or within a range defined by any two of the foregoing values. Such proximity to the nerve network enables a lower energy level of stimulation that is still suitable for stimulating the nerve network of the stomach. The lower energy level is suitable for stimulating the nerve networks but is not suitable for stimulating, for example, muscle contractions.

In some embodiments, delivering a first series of electrical stimulations includes sending electrical signals, via the temporary gastric or other GI tract stimulator, to the stomach (or other location in the GI tract) of the patient. The electrical signals may be sent via a plurality of electrodes contained or incorporated in the temporary gastric stimulator. The electrodes may be stimulation electrodes. The first series of electrical stimulations may include stimulations that are all the same energy level, intensity, duration, type (e.g., pulse versus continuous stimulation), frequency and/or amplitude. Additionally, and/or alternatively, the first series of electrical stimulations may include stimulations that are not all the same energy level, intensity, duration, type, frequency and/or amplitude as each other. The first series of electrical stimulations may include only one electrical stimulation or may include a plurality of stimulations, such as two, three, four, five, seven, ten, twelve, and so on.

In some embodiments, assessing whether there is improvement in GI symptoms of the patient includes self-reporting by the patient. In some embodiments, self-reporting may be in the form of a scored GI symptom diary including upper, mid and lower gut symptoms. Electrical parameters for the gastric stimulation therapy are refined through progressive monitoring and assessing of GI symptoms using the disclosed diagnostic modalities. Successful prolonged control of the symptoms of GI dysfunction via mucosal temporary gastric stimulator implantation indicates the high likelihood of a successful transition to permanent implantation of a serosal gastric stimulator device. Self-reporting of symptoms by the patient will be the most synonymous or correlative to whether there has been any improvement in GI symptoms as a result of gastric electrical stimulation.

Although not directly synonymous or correlative to improvement in GI symptoms, other markers may be monitored and/or measured as part of assessing whether there is improvement in GI symptoms experienced by the patient. These markers may be monitored and measured alongside the patient's self-reporting of GI symptoms. These markers should be assessed in light of the patient's self-reporting as each patient's experience is unique to that patient. Further, though the measurements of various markers may indicate improvement, the primary indication of improvement should be the direct experience of each individual patient.

For example, in some embodiments, improvement in the GI symptoms experienced by the patient means, for example, a one-point improvement in symptom scoring. In some embodiments, improvement in the GI physiologic parameters that influence symptoms experienced by the patient may provide insight into whether the GI symptoms have actually improved. Improvement in the GI physiological parameters may mean, for example, a positive measured change in inflammatory markers (such as IL-6), improved electrical activity in the stomach of the patient and/or improved enteric measurements. In some embodiments, improvement in the GI physiologic parameters that influence symptoms experienced by the patient is measured using one or more of the diagnostic modalities (discussed more fully below).

In some embodiments, if there is not significant improvement in the GI symptoms of the patient, the method may include delivering a second series of electrical stimulations to the stomach or elsewhere in the GI tract. The second series of electrical stimulations may be of a different implantation site, current, frequency, waveform and/or on/off pulse duration than the first series of electrical stimulations. Delivering either the first and/or second series of electrical stimulations to the stomach of the patient enables stimulation and/or modulation of the vagus and related nerves. Modulation of the vagus/other autonomic nerves includes modifying the electrical signal pattern, electrical signals and/or messages sent from the ENS to the CNS. Such modulation of the vagus nerve (and the electrical signal pattern communicated to the CNS) thereby treats or improves the GI symptoms of the patient.

The gastrointestinal pathologies and/or dysfunctions that are effectively treated with the disclosed treatment methodologies include, but are not limited to, gastroparesis (diabetic and idiopathic), inflammatory bowel disease, pancreatitis, gastroesophageal reflux disease, irritable bowel syndrome, chronic constipation, Whipple procedure induced nausea/vomiting, pregnancy-induced nausea/vomiting, chemotherapy and/or therapeutic radiation induced nausea/vomiting. Vagal mediated pathologies that are effectively treated through the disclosed protocol of gastric electrical stimulation, but are not confined within the gastrointestinal organs include atherosclerosis and Parkinson's disease.

Also disclosed are kits that can be used in the disclosed methods. In some embodiments, a kit includes an endoscope; percutaneous endoscopic gastronomy (PEG) or similar tubing; electrogastrogram (EGG) equipment; and anchoring devices. In some embodiments, the EGG equipment includes at least one temporary gastric stimulator, a plurality of sensors, at least one receiver to receive electrical signals generated by the temporary gastric stimulator, and a display. The display may be configured to display the electrical signals received by the receiver and may include at least one processor configured to convert the electrical signal received by the receiver into a graphical representation to be displayed on the display. The anchoring devices may include one or more of mucosal clips, anchoring devices or sutures configured to maintain a position of the at least one temporary gastric stimulator in a patient's stomach. The anchoring devices may secure the temporary gastric stimulator in the patient's stomach. Additionally, and/or alternatively, the anchoring devices may secure electrodes of the temporary gastric stimulator to various locations within the patient's stomach.

Identification/Diagnostic Modalities

The following modalities may be used in conjunction with the disclosed methods to identify and/or diagnose a patient as both a patient in need of gastrointestinal dysfunction treatment and as a suitable candidate for gastric electrical stimulation. Additionally, these modalities may be used in conjunction with the disclosed methods to assess the gastrointestinal (GI) symptoms experienced by a patient. The GI symptoms experienced by the patient may be assessed prior to delivery of the first series of electrical stimulations; during the delivery of the first series of electrical stimulations; and/or after delivering the first series of electrical stimulations. The GI symptoms experienced by the patient may also be assessed before, during and/or after delivery of a second series of electrical stimulations.

GI Symptom Diary

Patients may present with any number of motility-like problems often involving gastrointestinal (GI), nutritional, autonomic and/or systemic symptoms, which sometimes include many non-gastrointestinal symptoms. The initial focus for bio-electric therapies is on sign symptoms (i.e., what symptoms are visibly presented) and findings that may respond to directed therapies. The GI symptoms may include vomiting, nausea, loss of appetite or filling up early, bloating, distension, and abdominal pain, among others and some patients have lower GI and GU symtpoms including constipation, diarrhea, frequent or infrequent urination. Many patients also have gastro-esophageal reflux/heart burn symptoms and others have diarrhea and/or constipation. Nutritional symptoms may include weight loss, fluctuations in weight, and in some cases, weight gain.

Patients may have tried several dietary changes without improving their GI and/or overall symptoms. Non-GI symptoms may include symptoms of autonomic nervous system disorders, including fainting, weakness, sweating, and heat/cold intolerance. Many patients also have migraine headaches, and some have known or suspected autoimmune diseases such as fibromyalgia or interstitial cystitis. Signs of disorders in the patients that present with at least some of the GI/nutritional symptoms above may include disorders in gastric emptying of solids and or liquids, with some patients having rapid rather than delayed gastric emptying, measured by any number of techniques.

Patients may have disordered motility measurements in not only the stomach but in other areas of the GI tract, including the esophagus, small bowel and/or colon/anorectum. Other patients may have disordered electrical activity of the stomach or other parts of the GI tract determined by several related electrical measurement techniques. Patients with these disorders may have abnormal biopsies of the GI track lumen or more commonly of the nerves and muscles of deeper GI layers. Associated with these findings can be evidence of systemic inflammation (found by any number of techniques), along with autoimmunity and GI-tract associated microbiome measurements.

Patients are requested to capture their self-reported GI symptoms, often on a daily basis, for a period of at least one month. This symptom history is utilized to determine nausea scores and vomiting scores and related mid and hind gut (GI and GU) scores. The patient symptom diary may also be used to track frequency, intensity and/or duration of other specific GI symptoms such as bloating, gastric reflux and diarrhea.

Patient reported nausea scores and vomiting scores are calculated as follows. Using FDA compliant patient reported outcome (PRO) scoring systems (0-4, none to worse) one can rate each of 5 cardinal symptoms: vomiting, nausea, anorexia/early satiety, bloating/distension, and abdominal pain. The frequency and severity of the symptoms are also assessed, although those may be average for each score. A one-point drop in any of the symptoms, or a one-point drop in the mean of all symptoms, is considered a significant response. Other similar symptoms scales exist, but in most cases a 20-25% change in symptoms is needed to represent a meaningful change. The same symptoms scale can be used for related symptoms such as dysphagia, reflux, diarrhea, constipation, or urinary difficulties, where 0 is no symptoms and 4 is the worst case of symptoms.

GI symptom severity and consistency are represented through the scoring system described above. As such, these metrics are used to determine the appropriateness for an individual patient to be further evaluated and treated with the disclosed GI therapeutic flowchart (see, for example, FIG. 6). Using the patient reported score above, mean symptoms are considered mild if 0-1, are moderate if 1-2 and severe if 3-4, on the five-point scale above. As a general rule, symptom scoring should meet or exceed the following minima for further progression of clinical evaluation and treatment. Patients that exhibit prolonged scoring of 3 or greater on any symptom or an average of at least 2 of any GI symptoms on the GI PRO scoring diaries are considered to possess GI dysfunction of sufficient severity to potentially warrant GES.

Diet and Medication Trials

Diet trials are intended to provide the general dietary parameters for the duration of the trial. The parameters may include general dietary composition and calories, duration, weight monitoring details, diet log, and include physiologic measurements such as electrical impedance and similar measures that correlate with body mass index (BMI).

The standard dietetic approach is a low volume, low fat, low protein meal with frequent feedings. Data show that classes of malnutrition—defined as A (none), B (mild), C (moderate) and/or D (severe)—makes no difference in the patient response to gastric stimulation.

The classes of medications trialed, and the physiologic mechanism behind each medication classification used, define the clinical logic behind single medication versus multiple/simultaneous medication trials. The duration of therapeutic trials, monitoring methods of trials and general level of trial success (with success usually being defined as either a percent change, for example 20% improvement, or a scale change, such as a one-point reduction in a 0-4 or 0-5 scale) are also important factors. The usual duration of a drug trial is about one month, at a minimum. To contrast with gastric stimulation, using the same definitions of success, with a one-point change in a 5-point scale, greater than 80% of patients undergoing temporary GES have an improvement of GI symptoms at 12 months.

Classes of medications used for GI motility disorders are:

Symptomatic drugs by class: phenothiazine like drugs, histamine receptors and muscarinic antagonists, as well as related drug.

Prokinetic drugs by class: D2/D3 blockers, 5 HT 3 and 5 HT 5 drugs, NK-1 drugs, BH4 drugs, Ghrelin agonists, motility receptor dugs, as well as immunotherapy and in some cases drugs that are of similar action but are now investigational.

Medical Imaging

Without a physical gross obstruction, most patients are identified as having dysfunction or 'functional' abnormalities of the pylorus. The pylorus is a distal region of the stomach ending in the pyloric sphincter, which acts as a gate between the stomach and the duodenum (the first part of the small intestine). Recent data has shown that patients with symptoms of gastroparesis often have measurable abnormalities of gastric, electrical, and mechanical function of the distal stomach, including the pylorus. For example, a baseline solid gastric emptying at 4 hours may be greater than 10% retention for delayed patients and less than 10% for non-delayed patients where gastric stimulation is applied and cluster of differentiation (CD) 117 inner less than 2.0 and CD 117 outer less than 2.0 per high power field (HFP) and S100 inner less than 10 and S100 outer less than 10 per HPF. These abnormalities can be modulated by gastric stimulation.

These measurements correlated with pyloric distensibility and since gastric abnormalities can be modified by gastric stimulation, the pyloric function can also be modified by gastric electrical stimulation. Other measures of gastric function, such as the breath test, are like gastric emptying tests. Related GI transit markers such as the Smart Pill™ may show abnormalities of the GI tract that may respond to bioelectric therapies such as GI stimulation. The normal range for transit time includes the following: gastric emptying (2-5 hours), small bowel transit (2-6 hours), colonic transit (10-59 hours) and whole gut transit (10-73 hours).

Gastric Emptying Tests and Motility Studies

Gastric emptying and motility studies measure the physiology of patents without notable gross anatomy abnormalities. They measure how quickly a meal empties from a stomach. They parallel patient reported GI symptoms meeting clinical standard of gastroparesis and there is a plurality of ways to measure the GI symptoms.

Gastric emptying tests (GET) are measured in two main ways. First by a radiolabeled meal (which is the gold standard) or second, by a carbon isotope meal which correlates reasonably well with radio-isotope meals. "Normal" GET measurements depend on what type of meal and how the GET is measured. Normal values exist for each meal and type. For example, normal may mean having less than 10% of a solid radiolabeled/standardized meal left at 4 hours after ingestion. Rapid emptying of a solid meal is <33% retention at 1 hour. Delayed liquid emptying is >50% retention at 1 hour. GET does not always correlate with GI symptoms, although in more severe symptoms it correlates better. The application of gastric electrical stimulation for gastric emptying is to look at the effect of the stimulation on the emptying test (i.e., on the rate of emptying). The effect also depends on the 'dose' of electrical stimulation delivered. Improved gastric emptying/motility is achieved when the neuro-electrical patterns of the stomach (or elsewhere in the GI tract) are within the normal physiologic parameters in terms of amplitude, frequency and cyclic responsiveness to hormonal signaling. For some patients, this may be achieved with lower energy delivery per electrical stimulation, while other patient may require higher energy delivery. The dose, therefore, may be patient specific.

High resolution esophageal manometry (HREM) measures esophageal motor function with multiple probes, thus giving many data points of pressure (and resistance) during a study. HREM is an improvement over established low resolution esophageal motility (EM). HREM is measured like conventional esophageal manometry, with a probe placed into the esophagus, usually through the nose. HREM is measured by a series of numbers/data points for pressure, resistance, and movement of bolus of solid and/or liquid in the esophagus. Currently, HREM numbers are calculated by a computer and compared with normal ranges. For example, a standardized system called the Chicago classification, now in its 4th version, may be used. There is no one number or value that is used to define "normal" and/or "abnormal". Rather the Chicago classification looks at a composite of many numbers for its classification. In that sense, the current HREM uses a version of artificial intelligence to make its determinations.

HREM measurements are one way of looking at esophageal symptoms which may or may not relate to gastric measurements. Gastric measurements are currently much more straightforward, with parameters like gastric emptying (defined as % of a meal remaining in the stomach), electrogastrography (EGG) or electrogram (EG) (defined in frequency, amplitude and/or propagation, whether fasting, resting, or in response to a meal or other stimuli and by other measures), all of which can be compared and correlated with patient reported outcomes (PROs) for GI symptoms, the latter of which are collected according to FDA standardized parameters. For example, gastric measurements may be compared and correlated to a patient's scored GI symptom diary.

The "normal" range for the following parameters for esophageal manometry were calculated: distal contractile integral (mean 1319.44, with a 5-95th percentile range [185.65-3407.60]); contractile front velocity (mean 3.98, 5-95th percentile range [2.40-6.50]); intrabolus pressure (mean 9.68, range [1.00-19.00]); contraction amplitude measured approximately 5 cm above the esophagogastric junction (EGJ) (mean 78.76, range [23.00-146.00]); contraction amplitude approximately 15 cm above the EGJ (mean 43.66, range [3.60-96.00]); transition zone (TZ) length (mean 1.34, range [0.00-5.63]); upper esophageal sphincter (UES) pressure (mean 81.63, range [19.50-165.10]); EGJ length (mean 2.97, range [2.17-4.00]); EGJ resting pressure (mean 29.35, range [8.95-51.40]); EGJ relaxation pressure (mean 16.79, range [1.00-39.35]); IRPs4 (mean 13.42, range [2.59-28.28]); and gastric pressure (mean 5.06, range [0.00-9.46]).

An electrogastrogram (EGG) measures the electrical activity of the stomach. If it is cutaneous/external/surface it is called an EGG. If not, as noted below, is called an electrogram (or EG). EG is generally obtained more directly on the stomach or other GI organ, such as on the mucosal and/or serosal linings. EG can detect areas and/or direction of gastric electrical signal propagation for specific areas of the gastric lining better than traditional EGG.

Frequency and amplitude of cyclic electrical waves/peaks from the gastric tissues are measured over a time of several minutes to multiple days. EGGs, or EGs, are typically measured using one or more cutaneous electrodes. Normal wave frequency is between 2.5-3.3 CPM (1 standard deviation from the normal mean). Normal amplitudes are not determined as amplitude depends on a number of technical factors. EGG may better correlate with/to GI symptoms than gastric emptying tests (GET). Like GET, the important measure/outcome with gastric electrical stimulation is to see if there are changes in the EGG resulting from the bioelectric therapy of gastric electrical stimulation.

Additional Measurements

A variety of markers can be measured and/or monitored to measure inflammation, which may be correlated to GI symptoms. For example, c-reactive protein (CRP), erythrocyte sedimentation rate (ESR), and/or antibodies, among other things, can be monitored and measured. CRP (normal <3 mg/ml for high sensitivity CRP); ESR, (normal <22 pg/ml for males and <29 for females pg/ml); or cytokines: (Cytokines: normal TNF-α 1.7-11.5 pg/ml, and IL-6 normal <9.3 pg/ml). Different normal ranges may occur depending on the technology used to measure and monitor; for example, if micro beads by Luminex are used, values may be different than that of other technologies.

Cytokines and, specifically, chemo-kines may also be monitored and measured. Cytokines and chemokines are inflammatory markers and may be correlated to GI symptoms experienced by a patient. The cytokines and chemokines may be monitored and measured simultaneously or separately from each other. Various values and/or measurements have been established (chemokine, normal vs. patients): IL-8 3.10 pg/ml±1.85 vs.29.77 pg/ml±19.59, p=0.0035. MCP-1 77.95 pg/ml±28.77 vs. 127.76 pg/ml±34.44, p=0.0022. MIP-1a 23.06 pg/ml±11.39 vs. 49.19 pg/ml±20.44, p=0.0047. MIP-1b 49.05 pg/ml±22.14 vs. 100.73 pg/ml 45.10, p=0.0087. Antibodies (ATBs) may also be monitored and measured and may be correlated to GI symptoms. Normal antibodies<0.02 on paraneoplastic analysis and GAD-65<5.

The autonomic nervous system (ANS) can be measured directly from organ function or indirectly as through an organ's performance of its function. An example of direct ANS measurement is heart rate variation, with respiration and skin temperature and blood flow through capillaries. Indirect measurements of the ANS take something like heart rate and use computer analysis of the variations in heart rate (called heart rate variability) to determine other aspects of ANS function.

Like the other measures, for example HREM, normal and abnormal ranges depend on what is being measured, how it is being measured, and how it is being analyzed. Normal and abnormal values exist for each system (for example, the ANS and the CNS), based on normal controls. Using a standardized system, for example, the normal vagus cholinergic function with EKG R to R interval percentage change with respiration is >5%. For sympathetic adrenergic postural adjustment ratio (using digital photophlethysmography) is a ratio of >28 (although there may be some adjustments for age) and normal percentage vasoconstriction (of the opposite extremity immersed in ice) to cold is >81%. Like EGG/EG and GET, the correlation of ANS with GI Symptoms is variable. However, just like those other measures, the usefulness of ANS in patients with GI symptoms is to see the effects on the ANS before and after gastric electric stimulation is applied.

Measuring the enteric anatomy is an additional metric and may be measured via a mucosal (e.g., stomach lining) biopsy. If the result is a full thickness biopsy, the symptoms of the patient may be treated directly. An abnormal biopsy would indicate a need for electrical stimulation therapy and/or treatment. A normal biopsy is to have no thin muscles, defined as <1 mm; normal trichrome with no fibrosis; CD-117 (normal 5-6 per HPF, a decrease in functional dyspepsia in approximately 3-4 HPF, and gastroparesis in approximately <2 HPF); S-100 (n>15 per HPF); CD 3, 4, 8, 20, 68 (normally <1); and mast cell tryptase (normal <1).

Hormones and other bioactive compounds may also be measured. Hormones such as insulin, amylin and glucagon may be abnormal in patients exhibiting symptoms of gastroparesis and/or other motility disorders. These levels may be abnormal in patients with pre-diabetes and/or diabetes, as well as in other patients who are not diabetic or pre-diabetic. These hormones, which have well defined normal ranges, can be measured at baseline and in response to additional and/or alternative therapies. FIG. 3 illustrates normal and abnormal physiological parameter ranges. FIG. 4 illustrates normal and abnormal ranges of various biomarkers indicative of inflammation.

Gut-Brain Axis

The gut-brain axis (GBA) consists of bidirectional communication between the central and the enteric nervous systems, linking emotional and cognitive centers of the brain with peripheral intestinal functions. Insights into the gut-brain crosstalk have revealed a complex communication system that not only ensures the proper maintenance of gastrointestinal homeostasis, but is likely to have multiple effects on affect, motivation, and higher cognitive functions. Broadly defined, the GBA includes the central nervous system (CNS), the neuroendocrine system, the neuroimmune systems, the hypothalamic-pituitary-adrenal axis (HPA axis), the autonomic nervous system (ANS), the enteric nervous system (ENS), the vagus nerve, and the gut microbiota.

The role of the GBA is to monitor and integrate gut functions as well as to link emotional and cognitive centers of the brain with peripheral intestinal functions and mechanisms such as immune activation, intestinal permeability, enteric reflex, and entero-endocrine signaling. The mechanisms underlying GBA communications involve neuro-immuno-endocrine mediators.

The ANS, with its sympathetic and parasympathetic limbs, drives both afferent signals (arising from the lumen and transmitted though enteric, spinal and vagus pathways) to the CNS, and efferent signals from the CNS to the intestinal wall. Environmental stress, as well as elevated systemic pro-inflammatory cytokines, activate the HPA axis that, through secretion of the corticotropin-releasing factor (CRF) from the hypothalamus, stimulates adrenocorticotropic hormone (ACTH) secretion from pituitary gland that, in turn, leads to cortisol release from the adrenal glands. Cortisol is a major stress hormone that affects many human organs, including the brain. Thus, both neural and hormonal lines of communication combine to allow the brain to influence the activities of intestinal functional effector cells, such as immune cells, epithelial cells, enteric neurons, smooth muscle cells, interstitial cells of Cajal and enterochromaffin cells. Modulating, or changing, the stress communications originating from the ENS enables modulating the response of the CNS. Modulating and/or changing the response from the CNS may enable treatment of a variety of gastrointestinal dysfunctions.

The ENS is one of the main divisions of the nervous system and consists of a mesh-like system of neurons that governs the function of the gastrointestinal system. The enteric nervous system makes use of more than 30 neurotransmitters, most of which are identical to the ones found in CNS, such as acetylcholine, dopamine, and serotonin. The ENS communicates to the CNS via the parasympathetic (e.g., via the vagus nerve) and sympathetic (e.g., via the prevertebral ganglia) nervous systems.

The vagus nerve represents the main component of the parasympathetic nervous system, which oversees a vast array of crucial bodily functions, including control of mood, immune response, digestion, and heart rate. It establishes one of the connections between the brain and the gastrointestinal tract and sends information about the state of the inner organs to the brain. The vagus nerve's efferent fibers, which account for 10-20% of the fibers, send signals "down" from the brain (CNS) to the gut (ENS). The vagus nerve's afferent nerve fibers, which account for 80-90% of the fibers, send signals "up" from the intestinal wall to the brain. The most important function of the vagus nerve is afferent, bringing information of the inner organs (e.g., the gut, liver, heart, and lungs) to the brain. The main communicating transmitter is cholinergic activation through nicotinic receptors.

The vagus nerve communicates or interfaces with the ENS at varying locations and connect to the ENS via interstitial cells of Cajal (ICC) and other cells. ICC are known to contribute to several important functions in the GI tract including: (a) generation of electrical slow wave activity, (b) coordination of pacemaker activity and active propagation of slow waves, (c) transduction of motor neural inputs from the enteric nervous system, and (d) mechanosensation to stretch of GI muscles. Slow waves in smooth muscle tissues are periodic oscillations of the cell membrane potential consisting of a rapid upstroke and a longer plateau phase followed by repolarization. These fluctuations have characteristic frequencies in each organ and in each animal, between approximately 3 and 50 cycles per minute. In the stomach, the greater curvature is thought to include the pacemaker region as signals generally originate from the body-antral junction. The vagus nerve is thought to primarily interface on the lesser curvature of the stomach. The fundus is believed to be electrically quiescent (i.e., without slow waves) and the body of the stomach is believed to be the source of slow waves generation.

Methods of Treating Gastrointestinal Dysfunction

FIG. 1 illustrates an example method of the present disclosure. In some embodiments, method 600 includes identifying and/or diagnosing a patient as a suitable candidate for gastric electrical stimulation (step 610). In some embodiments, identifying and/or diagnosing the patient as a suitable candidate includes using one or more diagnostic modalities (discussed more fully above). The one or more diagnostic modalities may include scoring of the patient's GI symptom diary; performing diet and/or medication trials; performing medical imaging of one or more target anatomies of the patient; and performing gastric emptying and motility tests.

Cutaneous electrogastrograms (EGG) may be obtained as part of, or in addition to, the gastric emptying and motility tests. Additionally, and/or alternatively, more direct electrograms (EG) (e.g., direct EG of an organ) may be obtained as part of, or in addition to, the gastric emptying and motility tests. Other markers and/or systems may also be monitored and measured in identifying the patient as a suitable candidate. For example, physiological markers of inflammation (e.g., c-reactive protein, antibodies, cytokines, etc.) may be monitored and measured.

In some embodiments, method 600 also includes placing a gastric stimulator in the stomach of the patient (step 620). The gastric stimulator may be a temporary gastric stimulator. The gastric stimulator may be a wired or a wireless device. The gastric stimulator may be placed in the greater curvature of the patient's stomach, near the junction of the body and pyloric antrum of the stomach. The greater curvature generally includes the pacemaker region of the stomach and is electrically active. Surprisingly, placement of the gastric stimulator in the greater curvature enables stimulation of the vagus nerve, which primarily interfaces with the lesser curvature of the stomach.

In some embodiments, the method 600 further includes delivering a first series of electrical stimulations to the stomach via the temporary gastric stimulator (step 630). The first series of electrical stimulations includes a first energy level, a first frequency, a first intensity, a first current, a first on/off pulse duration and/or a first waveform type. The first series of electrical stimulations enable stimulation of the vagus nerve. Targeting the stomach with electrical stimulations indirectly stimulates the vagus nerve as the nerves of the stomach intertwine and weave back into the vagus nerve, and thus the brain stem and the brain. Stimulation of the vagus nerve enables modulation of the nerve-conducted electrical pattern from the stomach to the brain.

In other words, stimulating the vagus nerve modulates the electrical signals (and, thus, the communications/messages) sent from the ENS to the CNS via the gut-brain axis. Modulating the electrical signals sent from the ENS to the CNS changes the messages being sent to the CNS from the ENS. Rather than irregular messages of abnormal strength and frequency reaching the CNS (which drives ineffective, pathogenic responses), physiologically appropriate signaling can be delivered to the CNS from the ENS, via the vagus nerve, which would promote functionally effective responses within the gastrointestinal complex. By changing the messages sent to the CNS from the ENS, the gastrointestinal dysfunction can be treated. The gastrointestinal dysfunction may be ameliorated, or progression of the gastrointestinal dysfunction may be halted or slowed.

In some embodiments, method 600 includes assessing the GI symptoms experienced by a patient for whether there has been any improvement (step 640). Assessing the GI symptoms experienced by the patient may include using one or more of the diagnostic modalities (discussed more fully above). Assessing the GI symptoms may also include obtaining one or more cutaneous EGG or direct organ EG. Other markers and/or systems may also be monitored and measured in assessing the GI symptoms experienced by the patient. For example, physiological markers of inflammation (e.g., c-reactive protein, antibodies, cytokines, etc.) may be monitored and measured. These same markers may also be monitored and measured to identify whether a patient is a suitable candidate for gastric electrical stimulation therapy. A one-point drop in any of the symptoms, or a one-point drop in the mean of all symptoms, is considered a significant response. The one-point drop may be in comparison to a scored GI symptom diary of the patient. Other similar symptoms scales exist, but in most cases a 20-25% change in symptoms is needed to represent a meaningful change.

In some embodiments, at least one biomarker indicative of inflammation is monitored and measured. The at least one biomarker indicative of inflammation may include, but is not limited to, IL-6, IL-8, C-Reactive Protein (CRP), erythrocyte sedimentation rate (ESR), TNF-$\alpha$, MCP-1, MCP-1a, MIP-1a, MI-1b, GAD-65 and/or various antibodies. The at least one biomarker may be monitored and measured before, during and/or after delivery of the first series of electrical stimulations.

Systemic inflammation, or high levels of inflammation, is known to cause a variety of downstream effects in the body and is linked to a variety of pathologies. For example, chronic inflammation is linked to heart disease and atherosclerosis. Inflammation, at any level, is partially influenced by the vagus nerves and vagal activity. Modulating vagal activity (via modulating the electrical signal patterns sent from the ENS to the CNS) may also modulate the body's inflammatory response. Thus, modulating the inflammatory signals sent along the vagus nerve may treat, or at the very least halt progression of, inflammatory diseases such as atherosclerosis. As described elsewhere herein, gastric electrical stimulation via the disclosed methods beneficially modulates the electrical signal patterns sent from the ENS to the CNS, thereby treating gastrointestinal dysfunctions in a patient. This same electrical signal pattern modulation via gastric electrical stimulations (in the stomach or elsewhere along the GI tract) thereby also treats atherosclerosis.

In some embodiments, at least one physiological parameter is monitored and measured. The at least one physiological parameter may be monitored and measured by one or more of high-resolution esophageal manometry (HREM), gastric emptying tests (GET), measuring autonomic nervous system (ANS) activity (e.g., heart rate) and/or electrogastrograms (EGG). The at least one physiological parameter may be monitored and measured before, during and/or after delivery the first series of electrical stimulations.

In some embodiments, method 600 also includes delivering a second series of electrical stimulations, based on the assessment of GI symptoms experienced by the patient (step 650). For example, a measurement of IL-8 of 29.77±19.59 would be a deviation from the normal IL-8 range (3.10±1.85). This measurement may influence the parameters of the second series of electrical stimulations delivered to the patient (e.g., current, frequency, duration, intensity, etc.). The parameters would be chosen to meaningfully impact a subsequent measurement of IL-8.

The second series of electrical stimulations may be the same as the first series of electrical stimulations. The second series of electrical stimulations may be different than the first series of electrical stimulations, where the difference is one or more of current, intensity, on/off pulse durations, waveform type (e.g., pulsed or continuous stimulation), implantation site and/or frequency. Alternatively, based on the assessment of GI symptoms experienced by the patient, the method 600 includes implanting a permanent gastric stimulator. The permanent gastric stimulator may be the same stimulator as the temporary gastric stimulator. The placement of the permanent gastric stimulator may be the same as the temporary gastric stimulator (e.g., in the greater curvature of the stomach).

Figure 6:
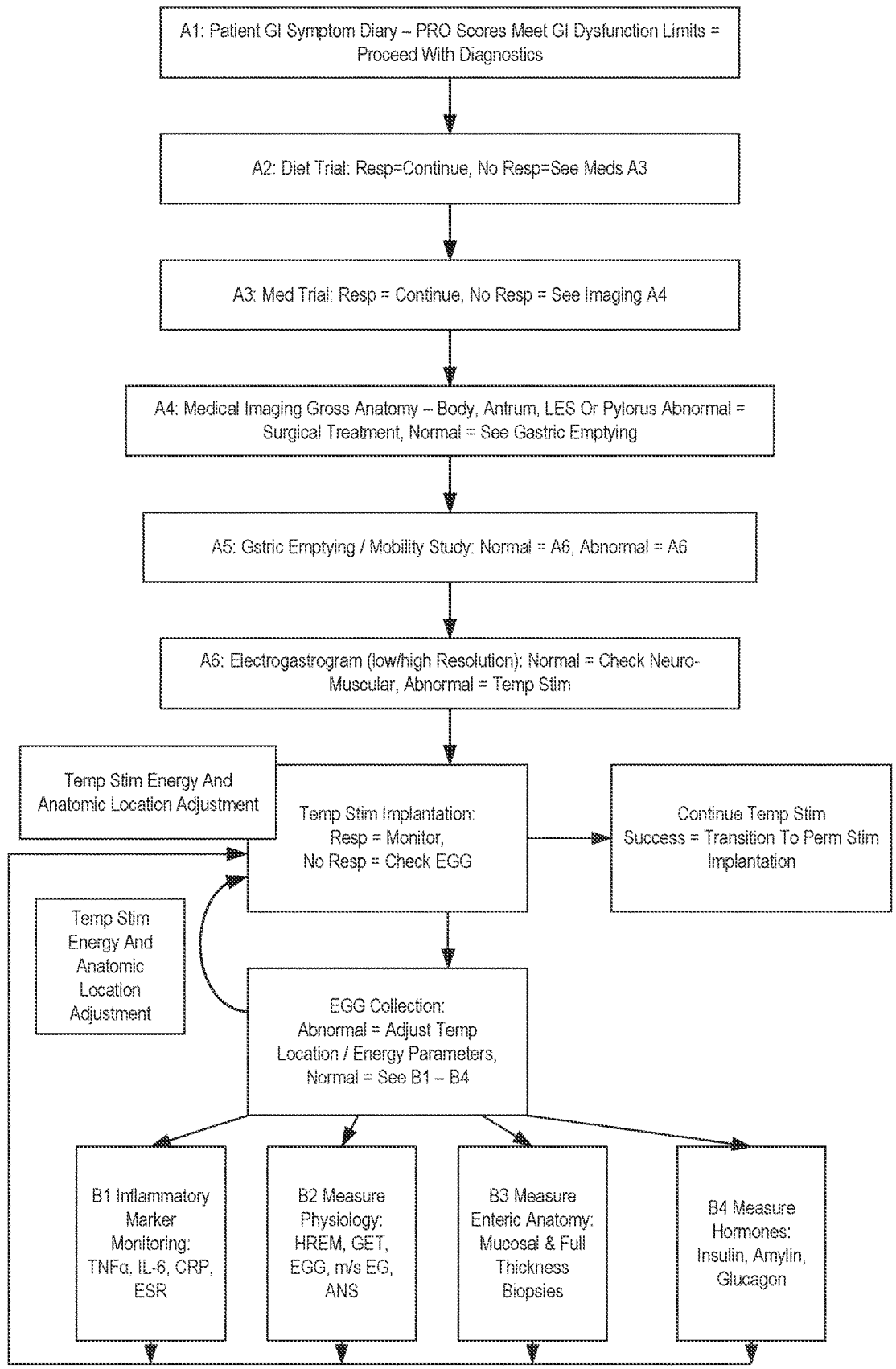
FIG. 6 is a flowchart that illustrates an example method.

FIG. 6 illustrates another example method. Specifically, FIG. 6 illustrates the various diagnostic modalities (A1-A6) that are performed and evaluated in addition to the delivery of electrical stimulations in treating gastrointestinal dysfunction in a patient. FIG. 6 also illustrates obtaining EGG measurements, both before and after temporary gastric electrical stimulation. The parameters for initial gastric electrical stimulation are based on the obtained EGG measurements prior to implementation. The parameters for a second round of gastric electrical stimulation are based on the obtained EGG measurements after initial gastric electrical stimulation. Also illustrated are measured physiological markers and inflammatory markers.

Figure 7:
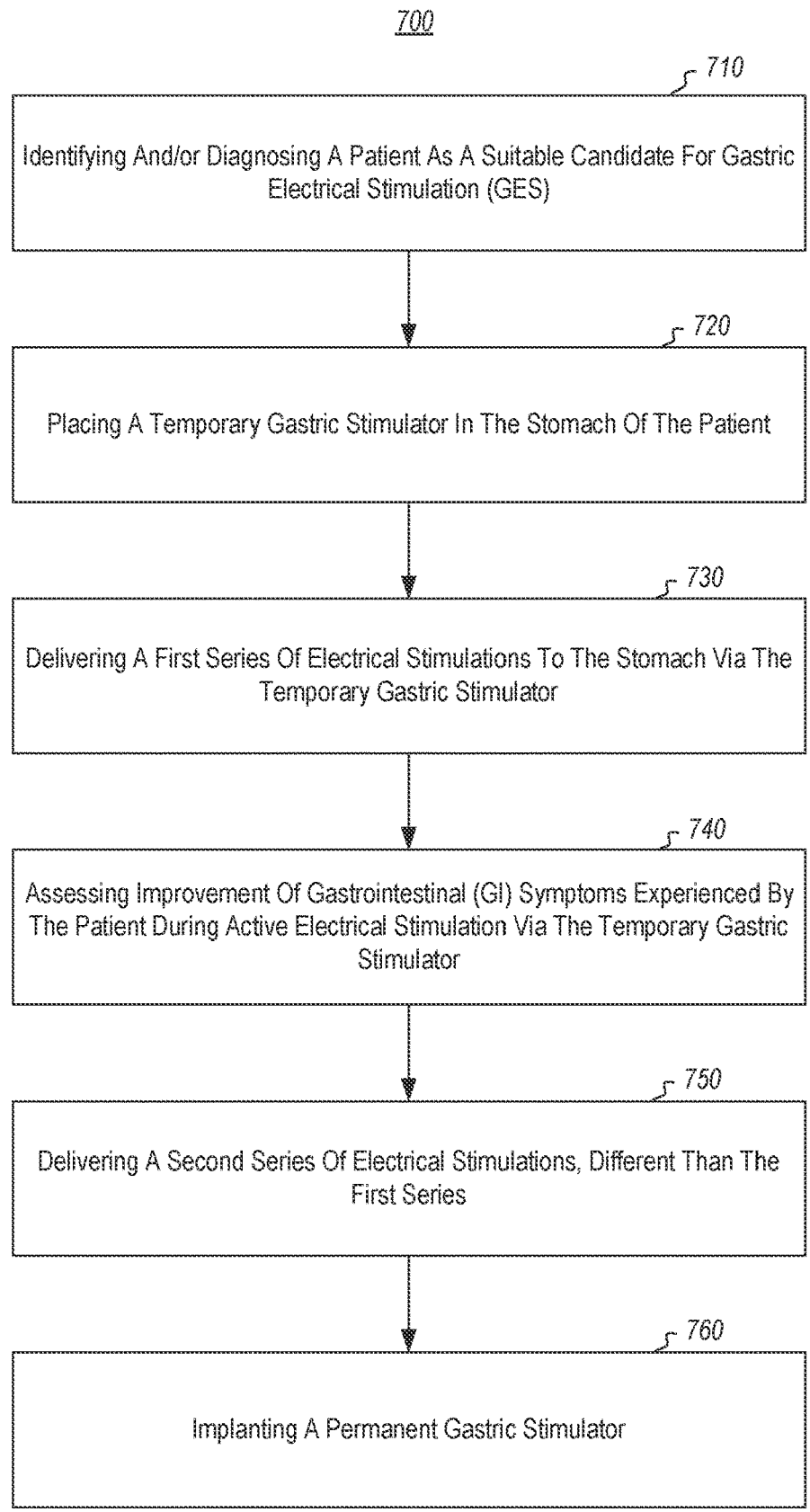
FIG. 7 is a flowchart that illustrates another example method.

FIG. 7 illustrates another example method of the present disclosure. In some embodiments, method 700 includes identifying and/or diagnosing a patient as a suitable candidate for gastric electrical stimulation (step 710). In some embodiments, identifying and/or diagnosing the patient as a suitable candidate includes using one or more diagnostic modalities (discussed more fully above). Additionally, and/or alternatively, physiological markers and markers of inflammation may also be monitored and/or measured in identifying a patient as a suitable candidate.

In some embodiments, method 700 also includes placing a gastric stimulator in the stomach of the patient (step 720). The gastric stimulator may be a temporary gastric stimulator and may be placed in the stomach of the patient endoscopically. The gastric stimulator may be placed at various locations within the stomach of the patient. For example, the gastric stimulator may be placed in the greater curvature of the patient's stomach. The gastric stimulator may be placed near the junction of the body and pyloric antrum of the stomach. The greater curvature generally includes the pacemaker region of the stomach and is electrically active. Surprisingly, placement of the gastric stimulator in the greater curvature enables stimulation of the vagus nerve, which primarily interfaces with the lesser curvature of the stomach.

In some embodiments, the method 700 further includes delivering a first series of electrical stimulations to the stomach via the temporary gastric stimulator (step 730). The first series of electrical stimulations include a first implantation site, a first current, a first frequency, a first on/off pulse duration and/or a first waveform type. The first series of electrical stimulations enable stimulation of the vagus nerve. Stimulation of the vagus nerve enables modulation of the nerve-conducted electrical pattern from the stomach to the brain. In other words, stimulating the vagus nerve modulates the electrical signals (and, thus, the communications) sent from the ENS to the CNS via the gut-brain axis.

In some embodiments, method 700 includes assessing the GI symptoms experienced by a patient for any improvement (step 740). Assessing the GI symptoms experienced by the patient may include using one or more of the diagnostic modalities (discussed more fully above). Additionally, and/or alternatively, physiological markers and markers of inflammation may also be monitored and/or measured in assessing the GI symptoms experienced by a patient.

In some embodiments, method 700 also includes delivering a second series of electrical stimulations, based on the assessment of GI symptoms experienced by the patient (step 750). The second series of electrical stimulations may be the same as the first series of electrical stimulations. The second series of electrical stimulations may be different than the first series of electrical stimulations, where the difference is one or more of energy level, intensity, duration, type (e.g., pulsed or continuous stimulation), frequency and/or amplitude.

In some embodiments, method 700 further includes, based on the assessment of GI symptoms experienced by the patient, implanting a permanent gastric stimulator in the stomach of the patient. The permanent gastric stimulator may be the same stimulator as the temporary gastric stimulator. The placement of the permanent gastric stimulator may be the same as the temporary gastric stimulator (e.g., in the greater curvature of the stomach). Alternatively, the placement of the permanent gastric stimulator may be different than the temporary gastric stimulator.

EXAMPLES

Example 1—Known Inflammation

A 32-year-old Caucasian female presented with a 2-year history of gradual onset bloating followed by nausea and vomiting which caused weight loss. The patient had several autoimmune signs, symptoms and markers that were abnormal and consistent with widespread inflammation.

After a trial of temporary, wired gastric stimulation the patient experienced improvement in GI symptoms and some of improvement in the autoimmune symptoms. She received a permanent gastric stimulator, and, after initial improvement, the patient started experiencing more GI symptoms with a recurrence of her autoimmune symptoms and elevated markers. Her gastric stimulation was adjusted to a higher energy level, with improvement in the GI symptoms, systemic symptoms and autoimmune markers over 6 months. The patient's symptoms, markers and gastric stimulator settings examined every 6 months and adjusted as needed.

Example 2—Diet Trial

A 46-year-old Asian male presented with a 1-year history of gradual onset abdominal pain and no weight loss. The patient tried several dietary changes, but none helped him improve.

After a trial of temporary gastric stimulation, the patient experienced improvement in GI symptoms and diet. No permanent gastric stimulator implanted but did not have long term improvement in his symptoms. He received wireless prolonged temporary gastric stimulation, with an improved and stabilized dietary intake and GI symptoms. He tried several newer medications and thought there was improvement. He had the prolonged temporary gastric stimulator device removed and has managed symptoms with the newer medications alone.

Example 3—Diet Trial

A 67-year-old Black female presented with a 5-year history of episodic severe nausea and vomiting. She had long term, insulin dependent diabetes mellitus, and the nausea and vomiting often resulted in diabetic ketoacidosis and hospitalization. The patient tried a number of dietary changes but none helped. She had been on a long-term prescription for metoclopramide but was unable to tolerate it due to neurological side effects. The patient attempted to obtain some investigational drugs but could not due to rapid gastric emptying (rather than delayed).

The patient trialed temporary gastric stimulation and experienced improvement in GI symptoms. Although she had some cyclic symptoms of nausea, she did not have to be hospitalized, which was an improvement. She had a permanent gastric stimulator implanted and found success but wanted to try a new medication and requested her gastric stimulator device be turned off. She did not respond well to the new medication and was hospitalized again. She requested having her gastric stimulator device turned back on and managed well alongside continued improvements in her glycemic control.

Example 4—Abnormal Enteric Anatomy

A 21-year-old White female presented with an 8-year history of chronic inability to gain weight. She had been diagnosed as having disordered eating with no response to behavioral therapy. She tried many GI medications for reflux, motility, and appetite stimulation without success. The patient trialed a nasal jejunal feed due to her low BMI. She stopped losing weight and, although still malnourished, agreed to a permanent jejunal tube. At the time of tube placement, she had a full thickness biopsy that showed markedly decreased Cajal cells with increased mast cells present in the GI tract.

The patient trialed temporary gastric stimulation, experienced improvement in GI symptoms and began to gain weight. She elected to have a long-term temporary gastric stimulator device implanted and subsequently decreased her jejunal feeds. She decided to have a pyloric intervention as her gastric/pyloric compliance was abnormal. At that time, she had an endoscopic full thickness biopsy which showed an increase in her Cajal cells and a decrease in mast cells. She decided to have a permanent gastric stimulator device and was monitored to assure that she obtained a normal weight.

Example 5—Abnormal NM Markers

A 29-year-old Hispanic male presented with a 3-year history of generalized GI motility and other troublesome symptoms. He had extensive evaluations including neurologic and autonomic testing. He was found to have an abnormal neuro muscular antibody that localized to the GI tract. He tried auto-immune medications but could not tolerate them. Autonomic and enteric testing revealed several abnormalities but did not lead to improvement in Gi symptoms.

The patient had a long term wireless temporary gastric stimulator device that resulted in improvement not only in GI Symptoms but in autonomic and enteric measures. He had his gastric stimulator device adjusted and further improved his autonomic and enteric measures. His GI and other symptoms were managed with a wireless gastric stimulator device, and regular autonomic and enteric profile testing with gastric stimulation amusements as indicated by the testing.

Example 6—Systemic Illness

An 8-year-old Caucasian female presented with lifelong failure to thrive. She had extensive in- and out-patient testing including exome analysis that was not specific for any known abnormality. Her GI markers were suggestive of inflammatory bowel disease but repeat testing was normal. However, her inflammatory markers were nonspecifically abnormal, and they tended to increase at times where the patient had some GI symptoms.

The patient had a long term wireless temporary gastric stimulator device that resulted in an ability to function better and improvement in her quality of life. Her systemic markers improved, and she received a permanent bio-electric implanated device.

Example 7

Patient presents with refractory GI symptoms. Patient presents with gastroenterology symptoms; gastroparesis; functional dyspepsia; unexplained nausea and vomiting; inflammatory bowel disease; and another inflammatory disorder.

The patient goes through the various identification/diagnostic modalities before applying therapeutic electrical stimulations. A diet trial is conducted with the patient; if there is a response, then the diet trial is continued. If no response (i.e., no improvement of GI symptoms), a medication trial is conducted with the patient. Similarly, if the patient responds to the medication, the medication trial is continued. Otherwise, the patient will be treated with electrical stimulations via a temporary gastric stimulator.

Before initial treatment with the temporary gastric stimulator, areas of the patient's gross anatomy may be imaged. For example, the lower esophageal sphincter and/or the pyloric sphincter may be imaged. If the images returned are abnormal, the patient may be treated using electrical stimulation. If the images returned are normal, the patient may go back to following the medication trial. Gastric emptying and motility tests may again be conducted on the patient presenting with abnormal gross anatomy images. Additionally, electrogastrograms (EGG) may be obtained.

Figure 2:
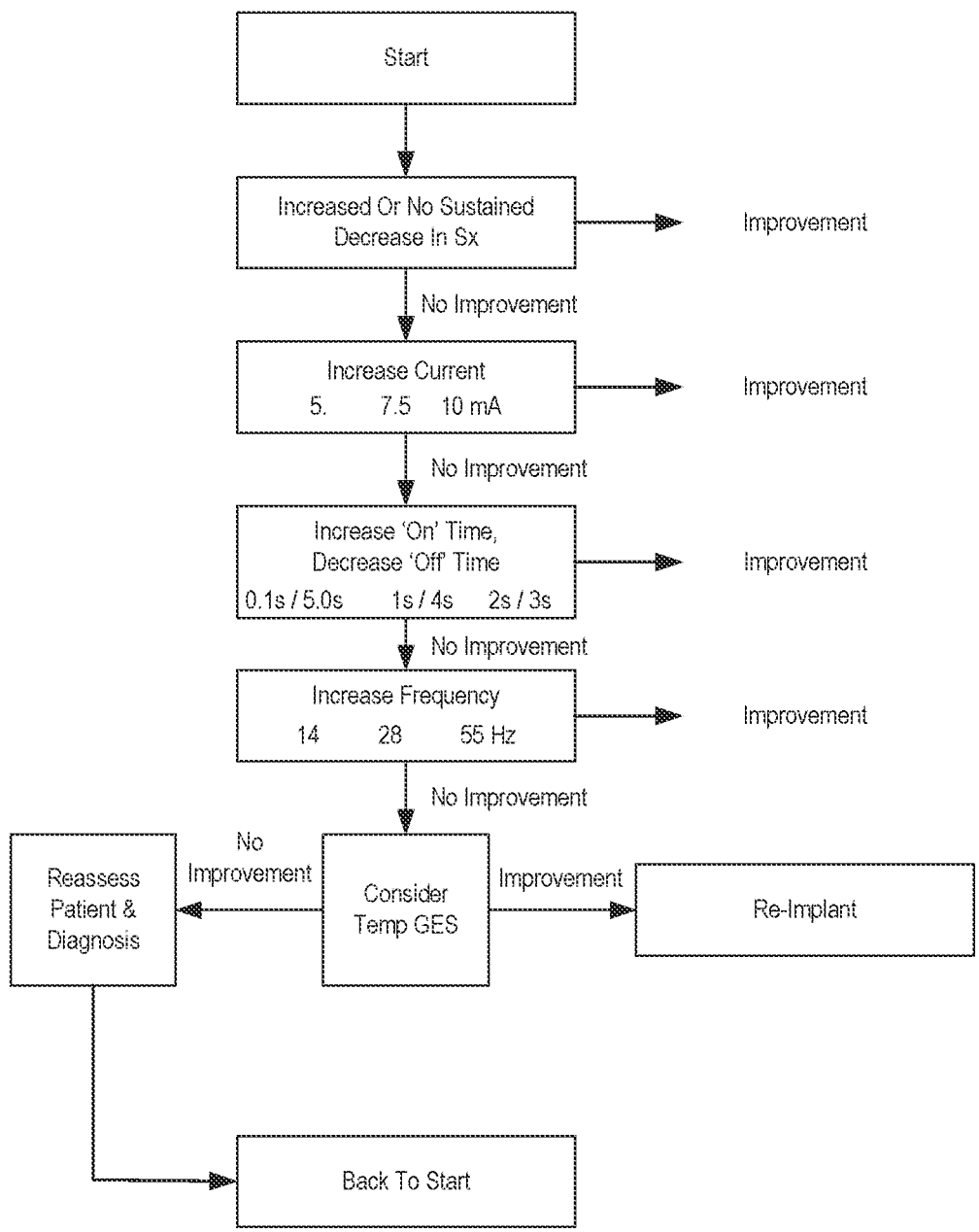
FIG. 2 is a flowchart that illustrates another example method of the present disclosure, illustrated as implemented in the stomach.

Following the identification/diagnostic modalities, and having identified the patient as a suitable candidate, therapeutic gastric electrical stimulations may be applied. A temporary gastric stimulator will be endoscopically implanted in the patient's stomach (at, for example, the greater curve) and activated. FIG. 2 illustrates an example method with example parameters that may be implemented during the gastric electrical stimulation. For example, electrical stimulation may be delivered to the patient. Note will be made of whether there has been an increase or no sustained decrease in symptoms (i.e., the symptoms will be assessed). Depending on whether there been an increase or no sustained decrease in symptoms, the output of the temporary gastric stimulator may be adjusted. For example, the current may be increased from 5 to 7.5 mA. The increase in current may correlate to an improvement in symptoms. If there is no improvement, the parameters of the electrical stimulation may again be modified (see, for example, FIG. 2). As another example, the "on" and/or "off" time can be adjusted, where the "on"/"off" time is shown in seconds. FIG. 5 illustrates typical gastric electrical stimulation output parameter settings for initial implantation, adjustment and maximum output settings. Continual adjustment can be made or there may be a transition to a permanent gastric electrical stimulator.

In assessing the symptoms, the patient's neuromuscular, neurologic and hormonal profiles will be evaluated (and re-evaluated). For example, this may include monitoring and measuring markers of inflammation (such as cytokines) and/or measuring hormone levels, specifically (e.g., insulin and/or amylin). There may also be a "stimulation trial" by endoscopically stimulating the mucosal, submucosal and/or serosal linings of the stomach via the temporary gastric electrical stimulator. The stimulation trial may occur at a plurality of locations in the stomach e.g., mucosal, submucosal linings, etc.). The response to the endoscopic stimulation may be monitored by monitoring the same symptoms and/or physiological parameters already discussed.

After electrical stimulation, at least one EGG will be obtained. In response to an abnormal EGG, the energy parameters of the electrical stimulation will be adjusted. An abnormal EGG includes a wave frequency outside of the normal 2.5-3.3 cycles-per-minute (cpm; 1 standard deviation from the mean). Additionally, and/or alternatively, the implantation location of the temporary gastric stimulator may be changed, and another EGG obtained. If a normal EGG is obtained (within the range of 2.5-3.3 cpm), the patient's inflammatory markers, hormones, enteric anatomy and/or physiological parameters may be measured as discussed more fully above. The inflammatory markers and clinical symptoms will be re-assessed and measured at prescribed time intervals.

The inflammatory markers and clinical symptoms may be re-assessed and measured, for example, once a week, weekly, twice a week, once a month, monthly, twice a month, three times a month, etc. If all diagnostics are consistently normal (e.g., all inflammatory, physiological and EGGs provide normal readings over a prescribed time, such as 6-months, one year, 18-months, etc.), the patient will undergo another diet trial with altered protocol. Gastric electrical stimulation treatment may be discontinued.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

As used herein, the term "treatment" refers to the medical management of a patient with the intent to cure, ameliorate, stabilize, or prophylactically treat a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that may be predisposed to the disease but has not yet been diagnosed as having it; (ii) inhibiting the disease, i.e., arresting its development; (iii) relieving the disease, i.e., causing regression of the disease; and (iv) reducing symptoms of the underlying disease, and/or that one or more of the underlying cellular, physiological, or biochemical causes or mechanisms causing the symptoms are reduced and/or eliminated. In one aspect, the subject is a mammal such as a primate, and, in a further aspect, the subject is a human.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A method for treating a gastrointestinal dysfunction in a patient in need thereof, the method comprising:
   identifying the patient as a suitable candidate for gastric or other gastrointestinal (GI) tract location electrical stimulation (GES);
   placing a temporary gastric stimulator in the stomach or other GI tract location of the patient;
   delivering a first series of electrical stimulation to the stomach or other GI tract location via the temporary gastric stimulator;
   measuring at least one biomarker indicative of inflammation selected from the group consisting of IL-6, IL-8, C-Reactive Protein (CRP), erythrocyte sedimentation rate (ESR), TNF-α, MCP-1, MCP-1a, MIP-1a, MI-1b, GAD-65, and antibodies;
   assessing whether there is an improvement in GI symptoms experienced by the patient during periods of active electrical stimulation via the temporary gastric stimulator;
   when there is GI symptom improvement in the patient during periods of active electrical stimulation via the temporary gastric stimulator, implanting a permanent gastric stimulator in the stomach or other GI tract location of the patient; and
   when there is not GI symptom improvement in the patient during periods of active electrical stimulation via the temporary gastric stimulator, obtaining an electrogastrogram (EGG) from a sensor positioned in the stomach or other GI tract location of the patient, and based on the obtained EGG:
   (i) delivering a second series of electrical stimulation to the stomach or other GI tract location via the temporary gastric stimulator, wherein the second series of electrical stimulation is at least one of a different current, different frequency, different on/off pulse duration, different waveform than the first electrical stimulation and/or different stimulator implantation site, wherein delivering a first and/or second electrical stimulation to the stomach indirectly stimulates the vagus nerve and other autonomic nerves, and
   (ii) implanting a permanent gastric stimulator in the stomach or other GI tract location of the patient.

2. The method of claim 1, wherein assessing GI symptom improvement comprises patient self-reporting.

3. The method of claim 1, wherein the sensor includes the previously placed temporary gastric stimulator.

4. The method of claim 1, wherein the permanent gastric stimulator is the temporary gastric stimulator.

5. The method of claim 1, wherein the sensor includes a cutaneous positioned sensor array.

6. The method of claim 1, wherein the sensor includes a mucosal positioned sensor array.

7. The method of claim 1, wherein the patient obtains GI symptom improvement from the first series of electrical stimulation delivered to the stomach via the temporary gastric stimulator, the method comprising implanting the permanent gastric stimulator in the stomach without delivering the second series of electrical stimulation.

8. The method of claim 1, wherein the patient dos not obtain GI symptom improvement from the first series of electrical stimulation delivered to the stomach via the temporary gastric stimulator, the method comprising (i) delivering the second series of electrical stimulation to the stomach or other GI tract location via the temporary gastric stimulator and (ii) implanting the permanent gastric stimulator in the stomach.

9. The method of claim 1, wherein the at least one biomarker is measured before, during and after delivering electrical stimulation by the temporary gastric stimulator and/or the permanent gastric stimulator.

10. A method for treating a gastrointestinal dysfunction in a patient in need thereof, the method comprising:
identifying the patient as a suitable candidate for gastric electrical stimulation (GES);
placing a temporary gastric stimulator in the stomach of the patient, wherein the temporary gastric stimulator is placed in a pacemaker region of the stomach, a greater curvature region of the stomach, or in a lesser curvature, fundus, and/or antrum of the stomach;
delivering a first series of electrical stimulation to the stomach via the temporary gastric stimulator;
assessing whether there is an improvement in GI symptoms experienced by the patient during periods of active electrical stimulation via the temporary gastric stimulator;
when there is GI symptom improvement in the patient during periods of active electrical stimulation via the temporary gastric stimulator, implanting a permanent gastric stimulator in the stomach; and
when there is not GI symptom improvement in the patient during periods of active electrical stimulation via the temporary gastric stimulator, obtaining an electrogastrogram (EGG) from a sensor positioned in the stomach of the patient, and based on the obtained EGG:
(i) delivering a second series of electrical stimulation to the stomach via the temporary gastric stimulator, wherein the second series of electrical stimulation is at least one of a different current, different frequency, different on/off pulse duration, different waveform than the first electrical stimulation and/or different stimulator implantation site, wherein delivering a first and/or second electrical stimulation to the stomach indirectly stimulates the vagus nerve and other autonomic nerves, and
(ii) implanting a permanent gastric stimulator in the stomach.

11. The method of claim 10, further comprising monitoring at least one physiological parameter.

12. The method of claim 11, wherein monitoring the at least one physiological parameter comprises monitoring by at least one of high-resolution esophageal manometry (HREM), gastric emptying tests (GET), autonomic nervous system (ANS) and/or electrogastrograms (EGG).

13. The method of claim 11, wherein the at least one physiological parameter is measured before, during and/or after delivering electrical stimulation by the temporary gastric stimulator and/or the permanent gastric stimulator.

14. The method of claim 10, wherein the temporary gastric stimulator is at least one of clipped, anchored or sutured into the stomach.

15. The method of claim 10, wherein the temporary gastric stimulator is placed at the mucosal surface of the stomach.

16. The method of claim 15, wherein the temporary gastric stimulator is placed within 0-15 mm of the nerve network of the mucosal lining of the stomach.

17. The method of claim 10, further comprising modulating the nerve-conducted electrical pattern from the stomach to the brain via the vagus nerve.

18. The method of claim 17, wherein modulating the nerve-conducted electrical pattern from the stomach to the brain, via the vagus nerve, treats at least one symptom of GI dysfunction of the patient.

19. The method of claim 18, wherein the at least one symptom of GI dysfunction treated is selected from the group consisting of:
gastroparesis;
inflammatory bowel disease;
pancreatitis;
gastroesophageal reflux disease;
irritable bowel syndrome;
chronic constipation;
pregnancy induced nausea/vomiting;
Parkinson's disease;
atherosclerosis;
spinal cord trauma;
Whipple procedure induced nausea/vomiting;
chemotherapy and/or therapeutic radiation induced nausea/vomiting; and
short gut and gut failure.

20. The method of claim 10, wherein delivering electrical stimulation to the stomach via the temporary gastric stimulator includes indirectly stimulating the vagus nerve via nerves of the stomach, wherein indirectly stimulating the vagus nerve provides GI symptom improvement in the patient, the method further including:
monitoring at least one GI symptom of the patient; and
adjusting the electrical stimulation for one or more of current, frequency, on/off pulse duration, stimulation pulse waveform, stimulator implantation site, or time.

21. The method of claim 20, wherein adjusting the electrical stimulation is based on a result of monitoring the at least one GI symptom of the patient.

22. The method of claim 20, further comprising:
monitoring at least one physiological parameter; and/or
monitoring at least one biomarker indicative of inflammation.

23. The method of claim 22, wherein adjusting the electrical stimulation is based on a result of monitoring the at least one physiological parameter and/or monitoring the at least one biomarker indicative of inflammation.

24. The method of claim 20, wherein indirectly stimulating the vagus nerve treats at least one symptom of GI dysfunction selected from the group consisting of:
gastroparesis;
inflammatory bowel disease;
pancreatitis;
gastroesophageal reflux disease;
irritable bowel syndrome;
chronic constipation;
pregnancy induced nausea/vomiting;
Parkinson's disease;
atherosclerosis;
spinal cord trauma;
Whipple procedure induced nausea/vomiting;
chemotherapy and/or therapeutic radiation induced nausea/vomiting; and
short gut and gut failure.

25. The method of claim 10, wherein the sensor includes the previously placed temporary gastric stimulator.

26. The method of claim 10, wherein the permanent gastric stimulator is the temporary gastric stimulator.

27. A method for treating a gastrointestinal dysfunction in a patient in need thereof, the method comprising:

identifying the patient as a suitable candidate for gastric or other gastrointestinal (GI) tract location electrical stimulation (GES) by at least two of:
  scoring a gastrointestinal (GI) symptom diary of the patient;
  implementing a diet trial;
  implementing a medication trial;
  performing medical imaging of one or more target anatomies of the patient;
  performing a gastric emptying and motility study;
  obtaining a cutaneous EGG of the patient's stomach; or
  obtaining a serosal EGG of the patient's stomach;
placing a temporary gastric stimulator in the stomach or other GI tract location of the patient;
delivering a first series of electrical stimulation to the stomach or other GI tract location via the temporary gastric stimulator;
assessing whether there is an improvement in GI symptoms experienced by the patient during periods of active electrical stimulation via the temporary gastric stimulator;
when there is GI symptom improvement in the patient during periods of active electrical stimulation via the temporary gastric stimulator, implanting a permanent gastric stimulator in the stomach or other GI tract location of the patient; and
when there is not GI symptom improvement in the patient during periods of active electrical stimulation via the temporary gastric stimulator, obtaining an electrogastrogram (EGG) from a sensor positioned in the stomach of the patient or other GI tract location of the patient, and based on the obtained EGG:
  (i) delivering a second series of electrical stimulation to the stomach or other GI tract location of the patient via the temporary gastric stimulator, wherein the second series of electrical stimulation is at least one of a different current, different frequency, different on/off pulse duration, different waveform than the first electrical stimulation and/or different stimulator implantation site, wherein delivering a first and/or second electrical stimulation to the stomach indirectly stimulates the vagus nerve and other autonomic nerves, and
  (ii) implanting a permanent gastric stimulator in the stomach or other GI tract location of the patient.

28. The method of claim 27, wherein assessing GI symptom improvement comprises patient self-reporting.

29. The method of claim 27, wherein the sensor includes the previously placed temporary gastric stimulator.

30. The method of claim 27, wherein the permanent gastric stimulator is the temporary gastric stimulator.

31. The method of claim 27, wherein the sensor includes a cutaneous positioned sensor array or a mucosal positioned sensor array.

* * * * *